United States Patent [19]

Melnick et al.

[11] 3,941,696

[45] Mar. 2, 1976

[54] STERILIZATION OF HOLDING TANKS AND TOILET BOWLS BY QUATERNARY COMPOUNDS

[75] Inventors: Joseph L. Melnick; Craig Wallis, both of Houston, Tex.

[73] Assignee: Baylor College of Medicine, Houston, Tex.

[22] Filed: Mar. 24, 1975

[21] Appl. No.: 561,447

Related U.S. Application Data

[63] Continuation of Ser. No. 426,793, Dec. 20, 1973, abandoned.

[52] U.S. Cl. .................... 210/62; 210/64; 424/159; 424/263; 424/329
[51] Int. Cl.[2] ............................................ C02B 3/06
[58] Field of Search .............................. 210/62, 64; 424/157–159, 263, 329

[56] References Cited
UNITED STATES PATENTS

| | | | |
|---|---|---|---|
| 2,793,973 | 5/1957 | Cheronis | 424/159 |
| 3,166,471 | 1/1965 | Gump et al. | 210/64 |

FOREIGN PATENTS OR APPLICATIONS

| | | | |
|---|---|---|---|
| 14,015 | 5/1895 | United Kingdom | 210/64 |
| 479,925 | 5/1936 | United Kingdom | 424/263 |

*Primary Examiner*—Thomas G. Wyse
*Attorney, Agent, or Firm*—James F. Weiler; William A. Stout; Dudley R. Dobie, Jr.

[57] ABSTRACT

Wastewaters heavily laden with organic compounds and containing viruses and other microbiological flora are sterilized and maintained sterile for prolonged periods of time by the addition of a base, such as lime, and a quaternary compound, preferably cetyl pyridinium chloride, in amounts to maintain the pH of the wastewaters at about 9–11, or higher, and with sufficient quaternary compound for suspended solids present. This prevents the formation of methane gases, which are tentative hazards in that they are inflammable, asphyxiant and narcotic. Similarly, toilets are rendered sterile by the addition of the base and quaternary compound so that, upon flushing, aerosols generated will not contain active infectious agents. All bacteria and fungi are inactivated under these basic conditions by the addition of quaternary compounds. Viruses are also inactivated under these basic conditions but only with quaternary compounds which contain the pyridinium moiety. The disclosure includes products for and methods of sterilizing wastewaters. A number of examples are given.

20 Claims, No Drawings

STERILIZATION OF HOLDING TANKS AND TOILET BOWLS BY QUATERNARY COMPOUNDS

This is a continuation of application Ser. No. 426,793, filed Dec. 20, 1973, now abandoned.

BACKGROUND OF THE INVENTION

At the present, holding tanks and ponds for wastewaters contaminated with bacteria, fungi and viruses are treated with a variety of agents which are only slightly bacteriostatic, are not virucidal, and generally mask the odor of the holding tanks and ponds. Some of the additives used for holding tanks are: phenols, zinc sulfate, and formaldehydes. Data have not been forthcoming to indicate the above additives will sterilize holding tanks and ponds laden with organic waste. Chlorine is ineffective in the presence of such increased loads of organic compounds; these readily deplete the activity of chlorine by converting this oxidizing agent to chloramines. Formaldehyde is not effective at normal pH of wastewaters. In our copending application, Ser. No. 392,962, however, formaldehyde is enhanced and becomes quite effective to sterilize wastewaters.

Similarly, additives used in toilet bowls usually are scented, colored compounds which are only weakly bactericidal and not at all virucidal. The flushing of toilets results in aerosolization of a percentage of the infectious agents excreted therein, which may account for transmission of infectious diseases to the next person using the toilet, or even to the next person entering the washroom in which the toilet is located.

Since the passage of the 1972 Water Pollution Control Act, vessels are no longer allowed to discharge their wastewaters overboard, but must retain these wastewaters in holding tanks for eventual removal from the vessel after arrival in port. At this point the wastewater contaminated with bacteria and viruses is physically removed and then disposed of, often overloading land-based sewage disposal plants. Active microbiologic flora from wastewater from boats may eventually find their way to surface or ground waters.

The prevention of contamination of our surface and ground waters of viruses, bacteria and fungi is of signal importance to our ecologic problems as related to public health. Similarly, the prevention of aerosolization of a percentage of infectious agents excreted in toilets upon the flushing of the toilets is of signal importance in the prevention of transmission of infectious diseases to the next person using the toilet, or even to the next person entering the washroom in which the toilet is located.

It would be highly advantageous, and the present invention is directed to, a product and method which inactivate bacteria, fungi and viruses contained in organic wastewaters, clean waters, and hard surfaces, which make the storage of wastewaters in tanks, ponds and the like safe and practical, and reduce the aerosolization of infectious agents which often contaminate toilets.

It is also of importance that holdings tanks aboard seagoing vessels and submarines, and airplanes, as well as other landbased holding tanks, be maintained odor free by sterilization of the wastewater. Holding tanks which are not maintained sterile will contain increasing amounts of methane synthesized by bacterial activity, which presents a hazard. It would be highly advantageous, and the present invention is directed to a product and method by which such wastewaters may be sterilized by heretofore ineffective compounds, quaternary compounds, but unexpectedly these quaternary compounds sterilize these wastewaters inactivating bacteria and fungi when the wastewaters are brought to pH 9-11 or greater, and that compounds of the pyridinium group, e.g., cetyl pyridinium chloride (CPC) will inactivate viruses as well as bacteria and fungi when the wastewaters are brought to this basic pH of 9-11 or greater.

Although it is known in the literature that quaternary compounds are more efficient bactericidal agents at higher pH levels than at neutral pH, none of the products presently on the market which contain quaternary compounds (mostly cetyl pyridinium chloride) are at basic pH levels. In fact, most are in the acid range, e.g., Cepacol, Scope, etc.

Although it is documented that the quats are more active at basic pH levels, the levels which have been tested are at pH 8 to 9, and furthermore they have been tested in clean water systems without organic loads. We have shown that in the presence of heavy organic loads cetyl pyridinium chloride at neutral pH levels is completely ineffective as a disinfectant, whereas at pH 10 it is an effective in the presence of organics as it is in the absence of organics. Thus, in the present invention, the adjustment to basic ph levels renders the quaternary resistant to inactivation by organics; this has never been reported.

SUMMARY

The present invention resides in the discovery that viruses and other microbiologic flora contained in wastewaters heavily laden with organic compounds, e.g., holding tanks, ponds, are rendered sterile, thus preventing the formation of methane gases which are tentative hazards, inflammable, asphyxiant and narcotic, by the addition of a base to bring the wastewaters to pH of 9-11 or greater and the addition of a quaternary compound in amounts sufficient to inactivate microbiologic flora contained therein.

Similarly, toilets can be rendered sterile so that upon flushing, aerosols generated will not contain active infectious agents.

In addition to inactivating bacteria and fungi in these wastewaters, by using a quaternary compound which contains the pyridinium moiety, preferably cetyl pyridinium chloride, viruses are inactivated when the wastewaters are brought to pH 9-11 or greater.

It is therefore an object of the present invention to provide for the sterilization of microbiologic flora contained in wastewaters heavily laden with organic compounds, e.g., holding tanks, ponds, toilets, thus preventing the formation of methane gases which are tentative hazards by the addition of a base to make the wastewaters basic pH of about 9-11 or greater, and a quaternary compound in an amount sufficient to inactivate the viruses and other microbiologic flora contained therein.

A further object of the present invention is markedly enhancing the sterilizing properties of quaternary compounds by making them basic so that when added to fluids or surfaces the final pH is in the range of 9-11 or higher and which effectively inactivate bacteria and fungi in wastewaters.

A further object of the present invention is the inactivation of bacteria, fungi and viruses in wastewaters in holding tanks, holding ponds, toilets, and the like, by the addition of quaternary compounds containing the pyridinium moeity and a base to render the waste waters of a final pH in the range of 9–11 or higher.

A further object of the present invention is the provision of a method and a product which renders toilets sterile so that upon flushing, aerosols generated will not contain active infectious agents.

A further object of the present invention is the provision of an effective, reliable, safe and inexpensive product and method by which holding tanks, ponds, toilets and the like are rendered sterile.

Other and further objects, features and advantages will be apparent from the abstract of the disclosure, the background of the invention, this summary, the description of the preferred embodiments and the claims.

DESCRIPTION OF THE PREFERRED EMBODIMENTS

The present invention is based upon the surprising discovery that bacteria, fungi, and viruses contained in organic wastewaters, clean waters, and hard surfaces in holding tanks, ponds, toilets and the like can be inactivated by the addition of normally ineffective quaternary compounds and a base which brings the wastewater to pH 9–11 or greater. The present invention is further based upon the surprising discovery that normally ineffective quaternary compounds which contain the pyridinium moiety or group can be utilized for inactivation of these agents when the wastewater is brought to pH 9–11 or higher.

The invention is applicable to all wastewaters, for example, wastewaters derived from holding tanks, which are mainly composed of fresh fecal and urine excreta, shredded toilet paper, soaps and detergents, and other matter disposed of in toilets; wastewaters containing animal excreta; and wastewaters containing industrial organics and the like. Accordingly, the terms "wastewater" or "wastewaters" as used herein include all wastewaters containing suspended solids which are or become contaminated with bacteria, fungi or viruses.

Any of the quaternary compounds may be used which include those listed in Example 3 below. If viruses are to be inactivated, only the pyridinium quaternary compounds when added to fluids of a pH of 9 and above are effective, which include cetyl pyridinium chloride (CPC) and those listed in Example 3 below. The other quaternary compounds, however, are quite effective to inactivate bacteria and fungi when the wastewater is made basic to pH 9 or higher.

Any suitable base may be used for adjusting the pH levels of wastewaters. These include lime (calcium hydroxide), sodium hydroxide, potassium hydroxide, calcium carbonate, sodium carbonate and the like.

The amount of quaternary compound introduced should be from 10 to 400 ppm per 1,000 ppm of suspended solids in the wastewater. The amount of base injected should be sufficient to establish a pH level 9–11 or higher, and preferably about 9.5 to 10.5.

In the case of holding tanks or ponds, the concentration of suspended solids is determined by any suitable means, such as the macerated effluent being driven into the holding tank or pond through an in-line turbidimeter thus establishing a turbidometric nomograph relating suspended solids to turbidity. Based on the amount of suspended solids being directed into the holding tank, the base and quaternary compound, such as lime and CPC, are automatically injected into the holding tank at a ratio within the range of 10 to 400 mg/l and a pH of 9.5 to 10.5, preferably 50 to 100 mg/l, and more preferably a ratio of 40 mg/l of CPC and a pH of 10.5 to 1000 mg/l of suspended solids. The holding tank is constantly stirred with a paddle-type mixer, and a pH probe monitors the holding tank to signal when the pH of the wastewaters in the holding tank decreases, for example, to pH 10.3. Additional base, such as lime, is automatically injected into the tank or pond to maintain the desired pH, for example, 10.5. In the case of toilets, the additives, a quaternary compound and base, preferably CPC and soda ash, are contained in the toilet tank to come into contact with water each time the tank refills, which releases a sufficient amount of CPC and base to give a final concentration of 20 mg/l of CPC and tank water that will attain a pH of 9.5–10.

In this specification and in the following examples bacteria and fungi were assayed by the methods described in "Antibiotics and Chemotherapeutic Agents in Clinical and Laboratory Practice" (Lorian, V., ed., Charles C. Thomas Publ., Springfield, Illinois, 1966). Viruses were assayed by the plaque-forming unit method (see "Diagnostic Procedures for Viral and Rickettsial Infections," 4th ed., Amer. Publ. Hlth. Assoc., 1969).

The following examples are given to illustrate representative embodiments of the present invention. Variations may be made, however, depending upon particular wastewater involved and conditions of use.

EXAMPLE 1

To a gallon of wastewater composed of fresh fecal matter, urine, soap and detergents, shredded paper and tap water (total suspended solids of 1000 mg/l), type 1 poliovirus was added to contain 100,000 infectious particles. The colony-forming units of bacteria and fungi at the initiation of this experiment were 1,000,000,000 per gallon. The wastewater was stirred with a paddle unit, and lime was added to attain a pH of 10.5. CPC was then added to attain 40 mg/l. After 24 hours at ambient temperature (20°–24°C), the wastewater was assayed for microbiological flora. No detectable bacteria, fungi or viruses were evident. A duplicate sample of 1 gallon of sewage processed without the addition of CPC, but maintaining the pH of the sewage at 10.5, manifested an excess of 500,000,000 assorted bacteria and fungi and 75,000 infectious virus particles after the 24 hour process period.

A duplicate sample with 40 mg/l of CPC but at the natural pH of the wastewater (pH 7.4), manifested an excess of 200,000,000 assorted bacteria and fungi and 90,000 infectious virus particles per gallon.

When the sample containing CPC at pH 10.5 was retested after one month, infectious agents still could not be detected, neither bacteria, nor fungi, nor viruses.

EXAMPLE 2

To a gallon of wastewater composed of fresh fecal matter, urine, soap and detergents, shredded paper and tap water (total suspended solids 5000 mg/l), type 1 poliovirus was added to contain 100,000 infectious particles. The colony-forming units of bacteria and fungi at the initiation of this experiment were 1,000,000,000 per gallon. The wastewater was stirred with a paddle unit, and lime was added to attain a pH of 10.5. CPC was then added to attain 200 mg/l. After 24 hours at ambient temperature, the wastewater was assayed for microbiological flora. No detectable bacteria, fungi or viruses were evident. A duplicate sample of 1 gallon of sewage processed without the addition of CPC, but only maintaining the pH of the sewage at 10.5, manifested an excess of 500,000,000 assorted bacteria and fungi and 75,000 infectious virus particles after the 24-hour process period.

A duplicate sample with 200 mg/l of CPC but at the natural pH of the wastewater (pH 7.4), manifested an excess of 200,000,000 assorted bacteria and fungi and 90,000 infectious virus particles per gallon.

When the sample containing CPC at pH 10.5 was retested after one month, again no detectable infectious agents could be detected.

EXAMPLE 3

To gallon samples of wastewater composed of fresh fecal matter, urine, soap and detergents, shredded paper and tap water (total suspended solids 1000 mg/l), type 1 poliovirus was added to contain 100,000 infectious particles. The colony-forming units of bacteria and fungi at the initiation of this experiment was 1,000,000,000 per gallon. The wastewater was stirred with a paddle unit, and lime was added to attain a pH of 10.5. Representative samples were treated with 40 mg/l Roccal (alkyldimethyl-benzylammonium chloride), Centrimide (cetyltrimethylammonium bromide), Ceepryn (cetylpyridinium bromide or chloride), Fixanol (tetradecylpyridinium bromide), Emulsept [N-(acylolaminoformylmethyl) pyridinium choride], cetramide (a mixture of $C_{12}$, $C_{14}$, $C_{16}$ alkyl trimethylammonium bromide), Arquad S (alkyltrimethylammonium chloride), Bradasol (phenoxyethyldimethyl-dodecylammonium bromide), Virac [acyl-cholaminoformylpyridinium chloride complexed with iodine (an iodophor)], Laurodin (4 aminoquinalidiniumlauryl acetate), or Triburon ( -iononetric lobisonium chloride). After 24 hours at ambient temperature the wastewater samples were assayed for microbiological flora. No bacteria or fungi were detectable in samples treated with the quaternary compounds at pH 10.5. Viruses were not detectable in those samples at pH 10.5 containing quaternary compounds with the pyridinium moiety, e.g. Ceepryn, Fixanol, Emulsept or Virac. On the other hand, viruses were present at high infectious levels in the pH 10.5 samples containing the other quaternary compounds not of the pyridinium moiety. (Roccal, Cetrimide, Arquad S, Bradasol, Laurodin, or Triburon).

Duplicate samples of wastewater treated with 40 mg/l of the above quaternary compounds, but not made basic with lime (natural pH of wastewater, 6.8), still contained large numbers of bacteria, fungi and viruses after the 24-hour holding period.

Additional control samples of wastewaters at ph 10.5 which were free of quaternary compounds manifested large numbers of bacteria, fungi and viruses after the 24-hour experimental period.

Essentially the same results were obtained when the experiment described in this example was performed with NaOH, soda ash or KOH for adjustment of the wastewater to pH 10.5.

EXAMPLE 4

Public toilet facilities were monitored for aerosolization of bacteria (including aerobic and anaerobic spores). Impingers were attached to the ceiling over the toilet bowl. Air was sucked into the impinger fluids at the rate of 1 cubic foot per minute. In one toilet stall, coliform bacteria isolated from impinger fluids at daily intervals for a period of one month averaged 150,000 coliforms per day. In the adjoining toilet stall which was monitored as described above, with the exception that the toilet tank was loaded with a device which maintained the toilet water at pH 10 with a final concentration of 20 ppm of CPC, the coliform count was less than 3 per day. In the next adjoining toilet monitored as described above, with toilet tank water containing CPC at the same concentration as used above but without pH control and with the natural pH of the toilet water (7.5), the coliform counts averaged 64,000 per day.

EXAMPLE 5

To an experimental toilet system, viruses were added to the toilet bowl to determine the amount of viruses aerosolized during flushing. Type 1 poliovirus was added to the bowl to contain 10,000,000 infectious particles, the level usually excreted per bowel movement by a person afflicted with an enteric virus disease, or by a healthy carrier of the virus. The bowl was flushed and the aerosol impinger collected 20 cubic feet of air immediately during and after the flushing. The impinger fluids (500 ml) were than concentrated (see Wallis, C. and Melnick, J. L. J. Viology 1:472–477, 1967) so that the final volume of 2 ml contained all the virus present in the original 500 ml used in the impinger. 72,000 infectious poliovirus particles were recovered from the air. When a duplicate experiment was conducted with toilet water containing 20 ppm of CPC and a final pH of 10 and the same level of virus as described above, no detectable virus was recovered from the concentrated impinger fluids. A third experiment carried out with toilet water containing only the base at pH 10 and no CPC, yielded 68,000 infectious particles, almost the same amount of virus in impinger fluids as described for the initial experiment. In a fourth experiment, toilet water was first treated with the same dose of CPC as described above, but without addition of a base; the natural pH of the toilet water was 7.5. Virus was again recovered from the impinger fluids, the count being 58,500 infectious particles.

EXAMPLE 6

Public toilet facilities were monitored for aerosolization of bacteria (including aerobic and anaerobic spores) as described in Example 4. In the toilet stalls, coliform bacteria isolated from impinger fluids at daily intervals for a period of one month averaged 200,000 coliforms per day. Adjoining stalls were monitored as described in Example 4, except the toilet tanks were loaded with a device which maintained the toilet tank water at pH 10 with a final concentration of 20 ppm of the quaternary compounds listed in Example 3. The coliform count in these representative toilets was less than 5 per day. In other toilets monitored in the same manner, with toilet tank water containing the quaternary compounds at the same concentration as used above but without pH control and at the natural pH of the toilet water (7.5), the coliform counts averaged 75,000 per day.

EXAMPLE 7

An experimental toilet system was monitored for aerosolization of viruses as described in Example 5. Duplicate experiments were conducted with toilet water containing 20 ppm of quaternary compounds with the pyridinium moiety (e.g. Ceepryn, Fixanol, Emulsept, and Virac). With a final pH of 10 and the same level of virus as described in Example 5, no detectable virus was recovered from the impinger fluids, even after concentration.

Another set of experiments carried out with toilet water at pH 10 but without the above quaternary compounds with the pyridinium moiety yielded almost the same amount of virus in impinger fluids as were detected in the initial experiment — 70,000 infectious particles.

In a fourth experiment, toilet water was first treated with the quaternary compounds listed above, but without addition of a base; the natural pH of the toilet water was 7.5. Virus was again recovered from the impinger fluids, the count being 60,000 infectious particles.

In all the foregoing examples, advantageously, the quaternary compounds and bases were added to the wastewater at ambient temperatures, no heating or cooling of the water being required.

The method of the invention comprises added to wastewaters 10 to 400 ppm of the quaternary compound and a base in an amount to bring the pH up to at least pH 9 and preferably 10.0 to 10.5. Preferably the quaternary compound should be pyridinium compound, for example CPC, to inactivate viruses as well as bacteria and fungi.

The amount of suspended solids should be determined, such as by an in-line turbidity meter and the pH should be maintained by a pH probe.

The wastewaters should be stirred, and preferably constantly, to assure complete dispersion of the quaternary compound and base in the wastewaters.

The quaternary compound and base may be added separately, in which event the base should be added first to bring the wastewater pH to 9 or greater. If desired, they may be added simultaneously and may be combined and added in combined form. They may be contained in a dispenser, for example, a perforate container for placing inside of toilet tanks so that contact with the refill tank water is made.

If desired, the tanks and ponds may be empty when the quaternary compounds and base are added. In this case, sufficient quaternary compound and base should be added to be effective for the expected volume of wastewater or capacity of the tank or pond for the solids suspended therein.

The terms "holding tanks" and "tanks" as used herein and in the claims are used in the broad meaning of these terms and include all ponds, receptacles, toilets, lakes and the like.

The present invention, therefore, is well suited and adapted to attain the objects and ends and has the advantages and features mentioned as well as others inherent therein.

While presently-preferred embodiments of the invention have been given for the purpose of disclosure, changes may be made to accommodate the conditions of use which are within the spirit of the invention as defined by the scope of the appended claims.

What is claimed is:

1. A method of sterilizing wastewater in tanks and the like, the wastewater having an organic load containing bacteria not inactivated by basicity alone and viruses comprising, adding 10 to 400 ppm liquid quaternary compound containing a pyridinium moiety to the wastewater for 1000 ppm suspended solids in the wastewater, and adding a liquid base to the wastewater to interact with said quaternary compound to cause said quaternary compound to inactivate said bacteria and viruses and in an amount sufficient to bring the wastewater to a pH of about 10.5.

2. The method of claim 1 where the quaternary compound is CPC

3. The method of claim 2 wherein the base is lime.

4. The method of claim 3 wherein the base and the quaternary compound are added simultaneously as a unitary liquid.

5. The method of claim 4 wherein 10 to 100 ppm quaternary compound is added to the wastewater.

6. The method of claim 4 wherein 50 to 100 ppm CPC is added to the wastewater.

7. The method of claim 3 wherein 10 to 100 ppm quaternay compound is added to the wastewater.

8. The method of claim 3 wherein 50 to 100 ppm CPC is added to the wastewater.

9. The method of claim 2 wherein the base and the quaternary compound are added simultaneously as a unitary liquid.

10. The method of claim 9 wherein 10 to 100 ppm quaternary compound is added to the wastewater.

11. The method of claim 9 wherein 50 to 100 ppm CPC is added to the wastewater.

12. The method of claim 2 wherein 10 to 100 ppm quaternary compound is added to the wastewater.

13. The method of claim 2 wherein 50 to 100 ppm CPC is added to the wastewater.

14. The method of claim 1 where the base is lime.

15. The method of claim 14 wherein the base and the quaternary compound are added simultaneously as a unitary liquid.

16. The method of claim 15 wherein 10 to 100 ppm quaternary compound is added to the wastewater.

17. The method of claim 14 wherein 10 to 100 ppm quaternary compound is added to the wastewater.

18. The method of claim 1 wherein the base and the quaternary compound are added simultaneously as a unitary liquid.

19. The method of claim 18 wherein 10 to 100 ppm quaternary compound is added to the wastewater.

20. The method of claim 1 wherein 10 to 100 ppm quaternary compound is added to the wastewater.

* * * * *